United States Patent
Cordia

Patent Number: 5,395,158
Date of Patent: Mar. 7, 1995

[54] HEAD SUPPORT AND FEEDING AID

[76] Inventor: James M. Cordia, Rte. 1, Box 211, Oakridge, Mo. 63769

[21] Appl. No.: 84,492

[22] Filed: Jul. 1, 1993

[51] Int. Cl.$^6$ ............................................. A47C 7/38
[52] U.S. Cl. .................................. 297/393; 297/464
[58] Field of Search ............... 128/869; 297/393, 391, 297/464, 410, 468, 353, DIG. 4, 440.1; 280/304.1

[56] References Cited

U.S. PATENT DOCUMENTS

| | | | |
|---|---|---|---|
| 2,638,293 | 5/1953 | Lindstrom | 297/393 X |
| 2,796,866 | 6/1957 | Cohen | 128/869 |
| 2,949,152 | 8/1960 | Hipps et al. | 297/464 X |
| 3,188,079 | 6/1965 | Boetcker et al. | 297/391 |
| 3,372,491 | 3/1968 | Morrison | 34/99 |
| 3,497,259 | 2/1970 | Sherfey | 297/391 |
| 3,730,589 | 5/1973 | Lane | 297/391 |
| 3,897,777 | 8/1975 | Morrison | 128/869 |
| 3,957,262 | 5/1976 | McReynolds | 297/391 X |
| 4,182,322 | 1/1980 | Miller | 128/869 |
| 4,227,740 | 10/1980 | East | 297/310 |
| 4,339,151 | 7/1982 | Riggs | 297/393 X |
| 4,589,407 | 5/1986 | Koledin et al. | 128/869 |
| 4,607,885 | 8/1986 | del Fierro | 128/869 X |
| 4,707,031 | 11/1987 | Meistrell | 297/393 |
| 4,989,836 | 2/1991 | Hudson, III et al. | 297/391 |

Primary Examiner—Kenneth J. Dorner
Assistant Examiner—Milton Nelson, Jr.
Attorney, Agent, or Firm—Jacobson, Price, Holman & Stern

[57] ABSTRACT

A head support and feeding aid is provided for a wheelchair patient whose head slumps forwardly when seated. A head band is attached to a frame on the wheelchair seat back by adjustable cords. By progressively adjusting the length of the cords, the head band progressively lifts the patient's head to a more and more upright position. The length of the cords is adjusted by releasable cord clamps behind the frame.

12 Claims, 3 Drawing Sheets

HEAD SUPPORT AND FEEDING AID

BACKGROUND OF THE INVENTION

This invention relates to an adjustable head support and feeding aid for patients who have lost muscle control in the back, shoulders or neck region to the extent that, when seated, the patient's head tends to slump forwardly towards or even onto the chest.

Many wheelchair patients, for example, lose the ability to control head movement. Shoulder and neck muscles become weak from non-movement and deteriorate rapidly to the extent that the patient is unable to hold the head upright and it tends to slump forwardly onto the chest. This condition is accelerated in older patients, particularly where the patient's condition has been weakened from prior medical problems such as stroke, or arthritis. Once the neck muscles weaken and the head drops forward, breathing becomes more difficult, and the intake of food and drink is impaired.

SUMMARY OF THE INVENTION

It is an object of the invention to provide a head support and feeding aid for patients of the above kind, which is useful in supporting the head in a more upright position and which with extended use may even be useful in restoring a degree of muscle power enabling the patient more readily to provide self-support for the head.

Another object of the invention is to provide a head support and feeding aid as described which can be adjusted in use, so that the patient's head can be brought gradually, over a period of time, to a more and more upright position.

A further object of the invention is to provide a head support and feeding aid in the form of an attachment which can be readily secured to a wheelchair or other seat.

A still further object of the invention is to provide a head support and feeding aid which is comfortable to wear and allows substantially unrestricted movements of the head other than in a forward direction.

Yet a further object of the invention is to provide a head support and feeding aid which is simple in design, economical to manufacture and easy to use.

In fulfillment of the above, a head support and feeding aid according to the invention, at least in a preferred embodiment thereof, comprises an arch-like support frame adapted to be attached to the back of a wheelchair or other seat so that the top of the frame extends substantially to the level of a seated patient's head, a head band of suitably soft and pliable material adapted to fit around the patient's forehead, an attachment cord or the like extending from each end of the head band through apertures in the frame, and releasable clamps on the cord behind the frame for adjusting the distance of the head band from the frame to suit the patient's head position and whereby the distance can be decreased to draw the patient's head progressively to a more and more upright position.

The frame may have adjustment means for height to suit a patient's height and head position and it may additionally have attachment means at its base for securing the frame to different size wheelchairs.

With extended use of the apparatus, a patient's head can be progressively brought to a more and more upright position with attendant beneficial effects.

Additional features and advantages of the invention will become apparent from the ensuing description and claims read in conjunction with the attached drawings.

DESCRIPTION OF PREFERRED EMBODIMENTS

Figure 1:
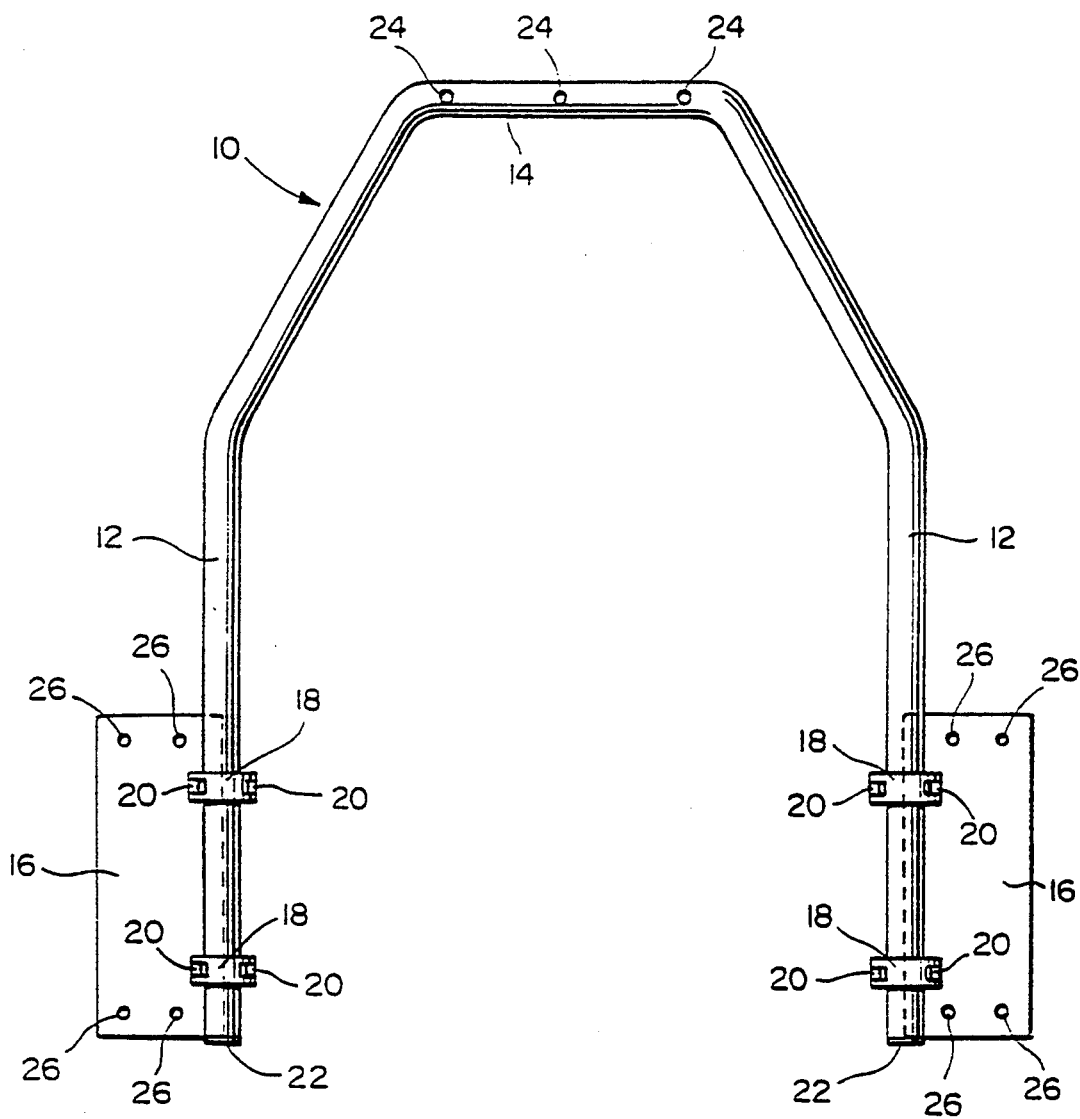
FIG. 1 is a rear elevational view of an attachment frame for a head support and feeding aid according to the invention.
Figure 2:
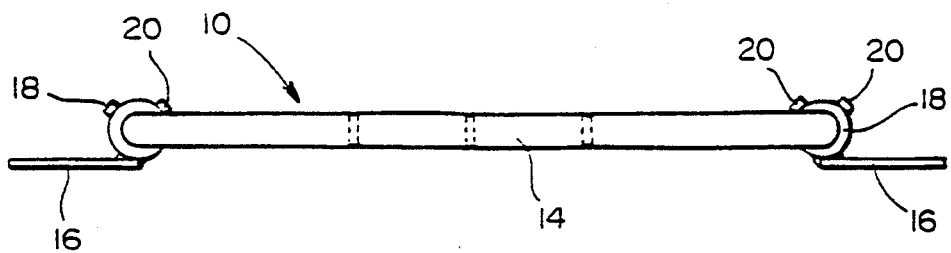
FIG. 2 is a plan view of the frame.
Figure 3:
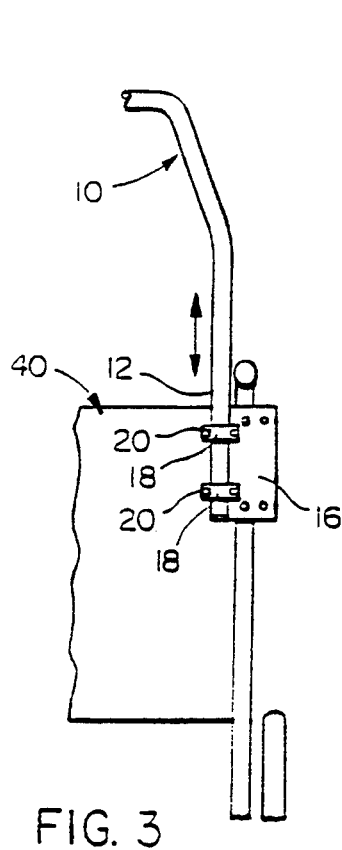
FIG. 3 is a rear elevational view of a part of a wheelchair with the frame attached.

An attachment frame 10 for a head support according to the invention is shown in detail in FIGS. 1 and 2. The frame is substantially in the shape of an arch with legs 12, and an upper cross-bar or limb 14. Preferably the frame is made of metal tubing or the like. At the bottom of each leg, the frame carries an attachment plate or bracket 16 mounted on the respective leg by a pair of collars 18 welded to the plate. The legs 12 are free to move lengthwise in the collars which are provided with tightening screws 20 for tightening down and locking against the frame. The bottom of each leg has a stop 22. Apertures 24 are provided through the limb 14 and inner and outer pairs of apertures 26 are provided in plates 16. (In an alternative embodiment, the frame 10 can be made of wood and can have attachment apertures at the bottom of each leg, eliminating the plates 16 and collars 18.)

Figure 4:
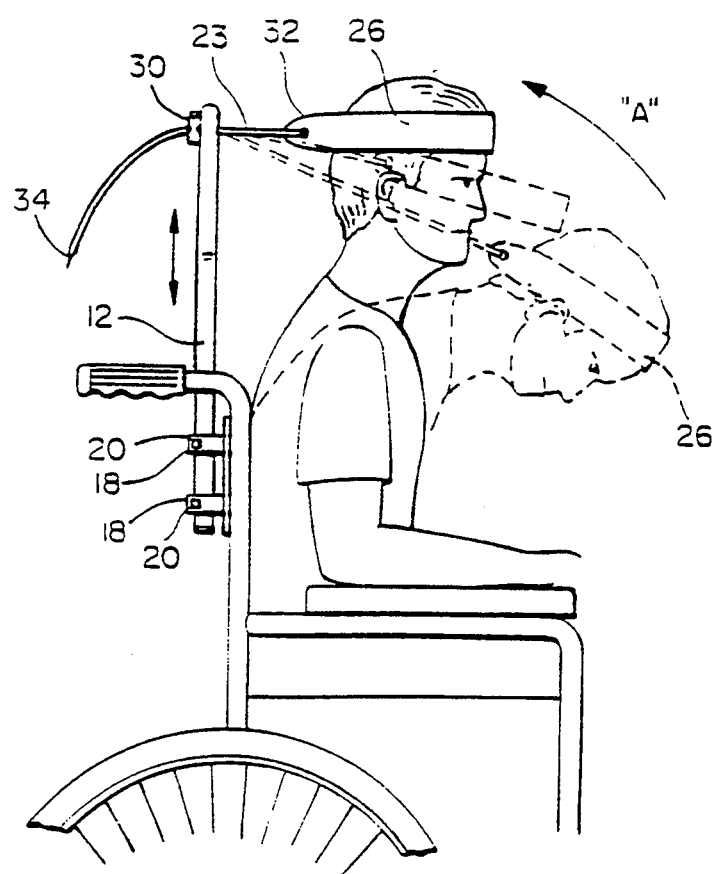
FIG. 4 is a side elevational view of the wheelchair showing the head support and feeding aid in use.
Figure 5:
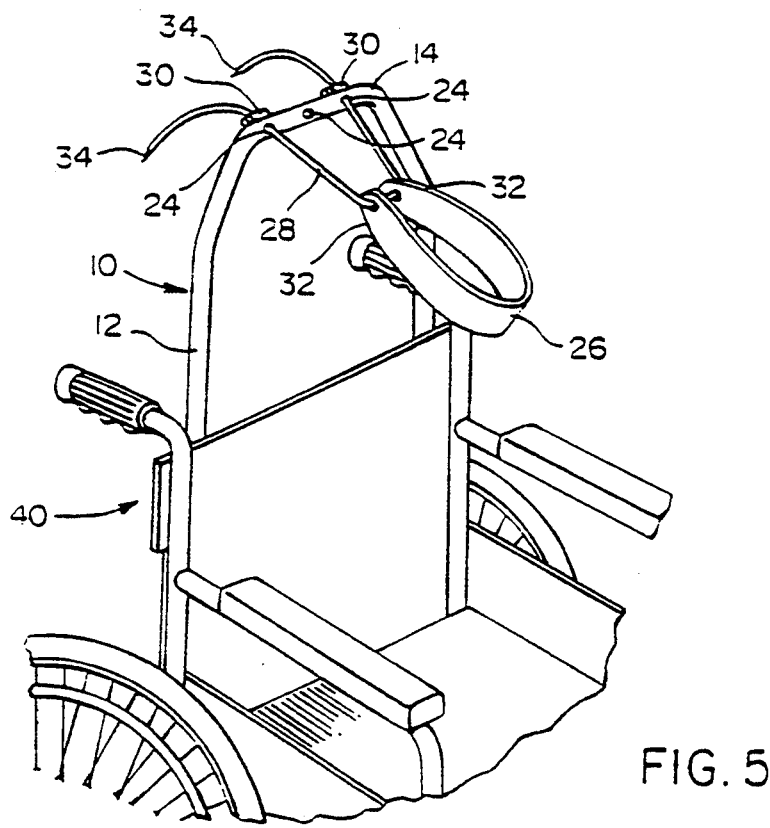
FIG. 5 is a front perspective view of the wheelchair and attached head support.

The apparatus further includes a head-band 26, see FIGS. 4 and 5, a cord 28, and releasable clamps 30 for the cord. The head-band may be of any suitable soft and flexible material for example foam rubber or the like in a fabric or terry-cloth cover, and has eyes 32 at each tapered end for the cord. The cord may comprise a length of plastic tubing with tapered ends 34. The ends of the cord are inserted from the front through the outer apertures 24 in frame 10, and are held in place behind the frame by the clamps 30. The clamps may, for example, comprise any known form of tube or cord clamp, for example, of the spring loaded plunger type. (In an alternative embodiment, the opposite ends of the head band may be secured to a single cord which is inserted through central aperture 24 and secured behind the frame by a single clamp.)

In use, the frame 10 is secured to the back of the wheelchair 40 using either the inner or outer set of apertures 20, depending on the width of the chair back. The height of the frame is adjusted in collars 18 so that the cross bar 14 is substantially level with a patient's forehead when the patient is seated upright, and the frame is locked in place using screws 20. Initially, the patient's head will drop forward to the dotted line position shown in FIG. 4. The head-band is fitted around the patient's forehead and cord 28 is initially adjusted using clamps 30 so that the head band exerts minimum upward pressure to the head in the direction of arrow A, for example lifting the head about one inch. Gradually, over a period of days, the cord can be adjusted through clamps 30 to reduce the distance between the head band and frame 10, thereby lifting the patient's head progressively in increments into a more and more upright position.

The head support is thus useful in helping to feed a patient and also to help the patient gradually regain an upright posture. Moreover, during use, the patient retains substantially unrestricted head movements other than in a downward direction. Extended use of the device assists in feeding the patient and also assists the patient in attaining improved breathing and posture. With extended use, the patient may even recover sufficient muscle control to sit unaided in a more upright position.

Figure 6:
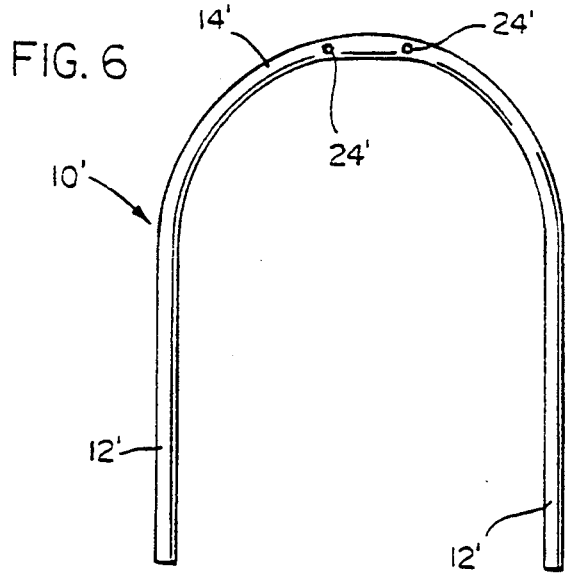
FIG. 6 is an elevational view of a simplified attachment frame.
Figure 7:
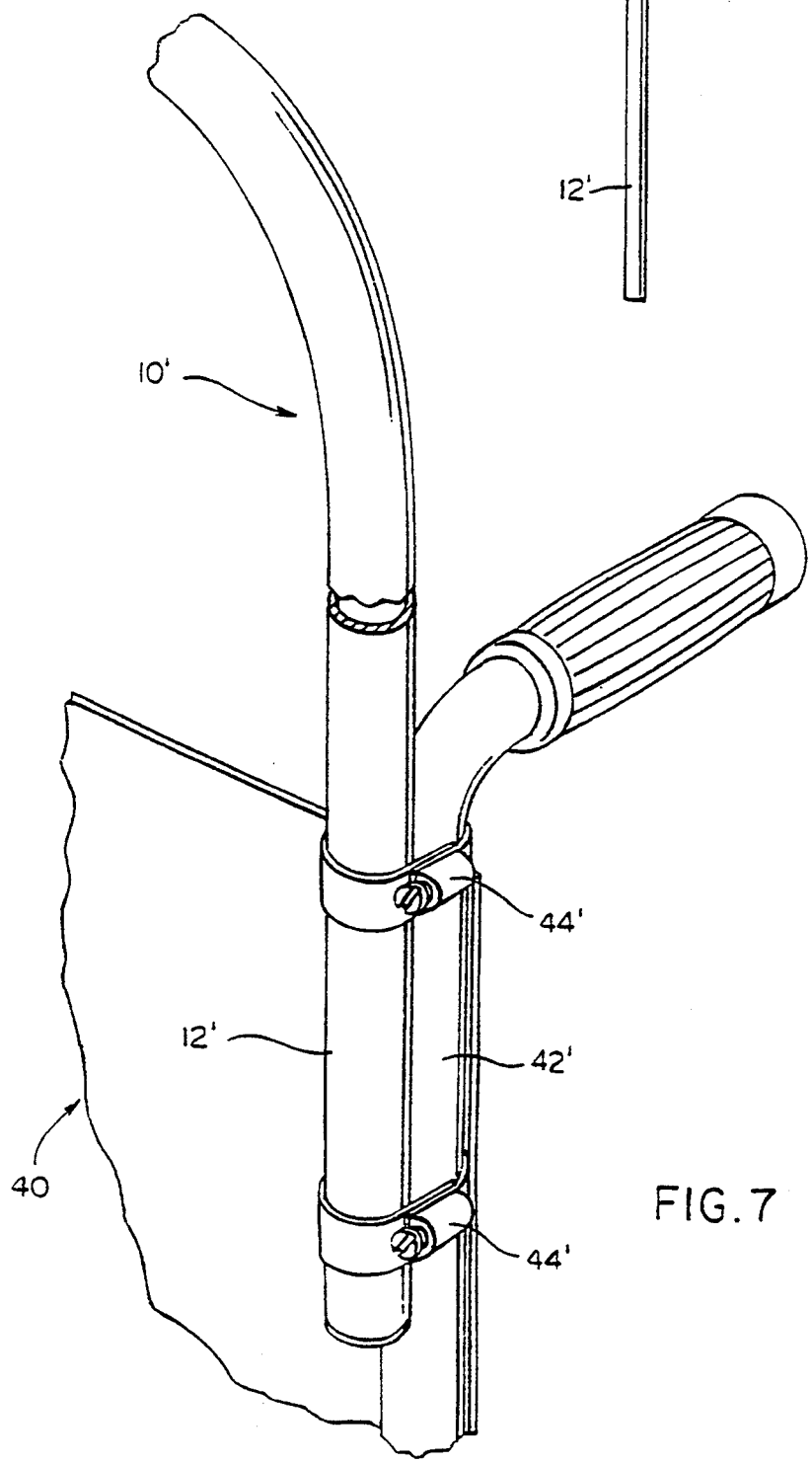
FIG. 7 is an enlarged perspective view of part of a wheelchair showing an attachment for the simplified frame.

FIGS. 6 and 7 show a simplified attachment frame 10' which has a smoother continuous curve-like arch with an upper limb 14', legs 12' and apertures 24' as previously The frame is again made of metal tubing and attaches to the side frames 42' of a wheelchair 40' by hose clips 44'. The hose clips again allow for height adjustment of frame 10'. The head band and cords are attached through apertures 24' as previously and the apparatus is used in like manner.

While only preferred embodiments of the invention have been described herein in detail, the invention is not limited thereby and modifications can be made within the scope of the attached claims.

I claim:

1. A head support and feeding aid for a patient whose head slumps forward when seated comprising a frame having a lower part for attachment to a seat back and an upper limb part, said upper limb part including aperture means formed therein, a head band for fitting around a patient's forehead, cord means extending from the head band for insertion through the aperture means in the upper limb part of the frame and releasable clamp means on the cord means for adjusting a length of the cord means between the head band and the frame thereby adjusting the distance of the head band from the frame to suit a patient's head position and whereby said length and said distance can be decreased progressively to draw a patient's head progressively to a more and more upright position.

2. A head support and feeding aid as claimed in claim 1, wherein the head band has opposite ends, wherein the cord means comprises a cord length extending from each end of the head band for insertion through a respective said aperture means in the upper cross bar part of the frame and wherein the releasable clamp means comprises a releasable clamp on each cord length.

3. A head support and feeding aid as claimed in claim 1, wherein the cord means comprises plastic tubing and wherein the releasable clamp means comprises at least one clamp.

4. A head support and feeding aid as claimed in claim 3, wherein the tubing has tapered ends.

5. A head support and feeding aid as claimed in claim 1, wherein the frame has depending legs, and attachment means for securing the legs to said seat back.

6. A head support and feeding aid as claimed in claim 5, wherein the attachment means includes height adjustment means for the frame.

7. A wheelchair for a patient whose head slumps forward when Seated, the wheelchair having a frame attached thereto, the frame having aperture means, a head band for fitting around a patient's forehead, cord means extending from the head band through the aperture means in the frame and releasable clamp means on the cord means for adjusting a length of the cord means between the head band and the frame whereby the head band, cord means and clamp means can be used as a head support for a patient for lifting the patient's head to a more upright position.

8. A wheelchair as claimed in claim 7, including height adjustment means for the frame.

9. A wheelchair as claimed in claim 9, utilizing a method of treating a patient whose head slumps forwardly when seated comprising seating the patient in said wheelchair, placing the head band around the patient's forehead and adjusting the length of the cord means between the head band and the frame by use of the clamp means so that the head band lifts the patient's head to a more upright position.

10. A wheelchair as claimed in claim 9, where the method of treating the patient further includes progressively adjusting the length of the cord means between the head band and the frame to progressively lift the patient's head to a more and more upright position.

11. A head support and feeding aid for a patient whose head slumps forward when seated comprising a frame having depending legs forming a lower part for attachment to a seat back and an upper limb formed with aperture means, attachment means for securing each of the legs of the frame to said seat back, the attachment means including height adjustment means for the frame so that the upper limb may be extended substantially vertically, the attachment means comprising a plate with plural apertures to receive connectors, the height adjustment means comprising at least one releasable locking collar on the plate in which a respective leg of the frame is received, a head band for fitting around a patient's forehead, cord means extending from the head band for insertion through the aperture means in the upper limb of the frame, and releasable clamp means on the cord means for adjusting a length of the cord means between the head band and the frame thereby adjusting the distance of the head band from the frame to suit a patient's head position and whereby said length and said distance can be decreased progressively to draw a patient's head progressively to a more and more upright position.

12. A head support and feeding aid for a patient whose head slumps forward when seated comprising a frame having depending legs forming a lower part for attachment to a side frame of a wheelchair and an upper limb formed with aperture means, attachment means for securing each of the legs of the frame to a side frame of a wheelchair, the attachment means including height adjustment means for the frame so that the upper limb may be extended substantially vertically the attachment means for each leg comprising at least one hose clamp for attaching each leg to said side frame of said wheelchair, a head band for fitting around a patient's forehead, cord means extending from the head band for insertion through the aperture means in the upper limb of the frame, and releasable clamp means on the cord means for adjusting a length of the cord means between the head band and the frame thereby adjusting the distance of the head band from the frame to suit a patient's head position and whereby said length and said distance can be decreased progressively to draw a patient's head progressively to a more and more upright position.

* * * * *